US00PP35691P3

(12) United States Plant Patent
Martin

(10) Patent No.: US PP35,691 P3
(45) Date of Patent: Mar. 12, 2024

(54) ***CANNABIS* PLANT NAMED 'POI'**

(50) Latin Name: *Cannabis sativa*
Varietal Denomination: POI

(71) Applicant: Umami Worldwide, LLC, Las Vegas, NV (US)

(72) Inventor: Chase Martin, Las Vegas, NV (US)

(73) Assignee: UMAMI WORLDWIDE, LLC, Las Vegas, NV (US)

( * ) Notice: Subject to any disclaimer, the term of this patent is extended or adjusted under 35 U.S.C. 154(b) by 0 days.

(21) Appl. No.: 17/950,094

(22) Filed: Sep. 21, 2022

(65) Prior Publication Data

US 2023/0093795 P1 Mar. 23, 2023

Related U.S. Application Data

(60) Provisional application No. 63/247,289, filed on Sep. 22, 2021.

(51) Int. Cl.
*A01H 5/00* (2018.01)
*A01H 6/28* (2018.01)

(52) U.S. Cl.
USPC ..... Plt./258
CPC ..... *A01H 6/28* (2018.05)

(58) Field of Classification Search
USPC ..... Plt./258, 263.1
CPC ... A01H 5/02; A01H 5/12; A01H 5/00; A01H 6/28
See application file for complete search history.

*Primary Examiner* — June Hwu
(74) *Attorney, Agent, or Firm* — Leonard R. Svensson; Intelink Law Group, P.C.

(57) ABSTRACT

The *Cannabis* cultivar 'POI' can be briefly characterized by massive purple, white, green, and yellow streaking resin-coated flowers. With massive flower clusters and very short internodal space, this cultivar is able to produce very high yields for both flower and hash production.

5 Drawing Sheets

Latin name of the genus and species: *Cannabis sativa.*
Variety denomination: 'POI'.

BACKGROUND OF THE INVENTION

The present invention relates to a new and distinct *Cannabis* cultivar designated 'POI'. This new cultivar is the result of controlled crosses between proprietary cultivars. 'POI' was asexually produced in Orange, CA via stem cuttings and cloning methods by the inventor. Asexual clones have been grown and tested indoors and in greenhouses and the properties are found to be transmissible by such asexual reproduction. The cultivar and its traits are stable through many generations of asexual propagation.

TAXONOMY AND NOMENCLATURE

*Cannabis*, more commonly known as marijuana, is a genus of flowering plants that includes at least three species, *Cannabis sativa, Cannabis indica*, and *Cannabis ruderalis* as determined by plant phenotypes and secondary metabolite profiles. In practice however, *Cannabis* nomenclature is often used incorrectly or interchangeably. *Cannabis* literature can be found referring to all *Cannabis* varieties as "*sativas*" or all cannabinoid producing plants as "*indicas*". Indeed, the promiscuous crosses of indoor *Cannabis* breeding programs have made it difficult to distinguish varieties, with most *Cannabis* being sold in the United States having features of both *sativa* and *indica* species.

Human cultivation history of *Cannabis* dates back 8000 years (Schultes, R E., 1970, Random thoughts and queries on the botany of *Cannabis*. Pages 11-38 in: CRB Joyce, and S H Curry eds., THE BOTANY AND CHEMISTRY OF

*CANNABIS*. J. & A. Churchill. London, England). Hemp cloth recovered in Europe dates back 6000 years (Small, E, Beckstead, H D, and Chan, A, 1975, The evolution of cannabinoid phenotypes in *Cannabis*, ECONOMIC BOTANY 29(3):219-232). The written record of the pharmacologic properties of *Cannabis* goes back more than 4000 years (Ti, H. 2737 BC. NEI JING SU WEN HUANG TI, Yellow Emperor's Classic on Internal Medicine; referred to without citation in Small et al. 1975 Supra).

The taxonomy and nomenclature of the highly variable genus *Cannabis* (Emboden, W A, 1974, ECONOMIC BOTANY 28(3):304-310; Small, E and Cronquist, A, 1976, TAXON 25(4):405-435; Small E and Cronquist, A, 1977, TAXON 26(1):110; Hillig, K W and Mahlberg, P G, 2004, American Journal of Botany 91(6):966-975), remains in question. This is in spite of the fact that its formal scientific name, *Cannabis sativa* L., assigned by Carolus Linneaus (Linnaeus, C, 1753, SPECIES PLANTARUM, 2:1027, Salvius, Stockholm, Facsimile edition, 1957-1959, Ray Society, London, U.K.), is one of the oldest established names in botanical history and is still accepted to this day. Another species in the genus, *Cannabis indica* Lam. was formally named somewhat later (de Lamarck, J B, 1785, ENCYCLOPEDIE METHODIQUE DE BOTANIQUE, 1(2):694-695), but is still very old in botanical history. In 1785, Jean-Baptiste Lamarck published a description of a second species of *Cannabis*, which he named *Cannabis indica*. Lamarck based his description of the newly named species on plant specimens collected in India. *C. indica* was described as relatively short, conical, and densely branched, whereas *C. sativa* was described as tall and laxly branched (Schultes R. E. et al, 1974, Harvard University Botanical Museum Leaflets, 23:337-367). *C. indica* plants were also described as having short, broad leaflets whereas those of *C. sativa* were characterized as relatively long and narrow (Anderson L. C., 1980, Harvard University Botanical Museum Leaflets, 28:61-69). *C. indica* plants conforming to Schultes' and Anderson's descriptions may have originated from the Hindu Kush mountain range. Because of the often harsh and variable (extremely cold winters, and warm summers) climate of those parts, *C. indica* is well-suited for cultivation in temperate climates.

Three other species names were proposed in the 1800s to distinguish plants with presumably different characteristics (*C. macrosperma* Stokes, *C. chinensis* Delile, *C. gigantean* Vilmorin), none of which are accepted today, although the epithet "*indica*" lives on as a subspecies of *C. sativa* (*C. sativa* ssp. *indica* Lam., Small and Cronquist 1976 Supra).

In the 20th century, two new names were added to the 50 liturgy of proposed *Cannabis* species: *C. ruderalis* Janischevsky and a hybrid, x *C. intersita* Sojak. (Small, E, Jui, P Y, and Lefkovitch, L P, 1976, SYSTEMATIC BOTANY 1(1): 67-84; Small and Cronquist 1976 Supra). Further, numerous names have been proposed for horticultural variants of *Cannabis* but as of 1976, "very few of these have been validly published as formal taxa under the International Code of Botanical Nomenclature" (Small and Cronquist 1976 Supra). Moreover, other recent work continues to focus on higher-order evolutionary relationships of the genus. *Cannabis* has been variously ascribed as belonging to mulberry family (Moraceae) (Engler, H G A, Ulmaceae, Moraceae and Urticaceae, pages 59-118 in: A. Engler and K. Prantl eds., 1889, DIE NATURLICHEN PFLANZENFAMILIEN 3(1). W. Engelmann, Leipzig, Germany; Judd, W S, Sanders, R W, and Donoghue, M J, 1994, HARVARD PAPERS IN BOTANY 5:1-51; Humphries, C J and Blackmore, S, A review of the classification of the Moraceae, pages 267-277 In: Crane and Blackmore 1989 id.); nettle family (Urticaceae) (Berg, C C, Systematics and phylogeny of the Urticales, pages 193-220, in: P. R. Crane and S. Blackmore eds., 1989, EVOLUTION, SYSTEMATIC, AND FOSSIL HISTORY OF THE HAMAMELIDAE, VOL. 2, HIGHER HAMAMELIDAE, Clarendon Press, Oxford, U.K.); and most recently in its own family with hops (Humulus), Cannabaceae, or hemp family (Sytsma, K J, et al, 2002, AMERICAN JOURNAL OF BOTANY 89(9): 1531-1546). While the work of Small and Cronquist 1976 Supra, seemed to effectively confine the genus to a single species with 2 subspecies (*C. sativa s., C. s. indica*), each with two varieties (*C. s. s.* var. *sativa, C. s. s.* var. *spontanea; C. s. i.* var. *indica, C. s. i.* var. *Kafiristanica*) largely on the basis of chemotaxonomy and interfertility of all forms, more recent work (Sytsma et al. 2002 Supra), proposes a two-species concept, resurrecting the binomial *C. indica* Lam. Since Sytsma et al. (2002) provides no key for discriminating between the species, the dichotomous key of Small and Cronquist (1976), which accounts for all forms in nature, whether wild or domesticated, is preferred to classify the characteristics of the plants.

BRIEF SUMMARY OF THE INVENTION

The present invention relates to a new and distinct *Cannabis* cultivar designated 'POI'.

'POI' is a poly hybrid cultivar. The mother is a mix of elite cultivars consisting of many varieties including Purple Payne Killer, Durban Poison, Gelato #41, and Motorbreath #15. The mother plant is a rare outlying phenotype that can yield 90+ grams/ft2 under LED lighting and test at over 30% THC. The father is the proprietary breeder stud 'Zuchi' described in co-pending Plant patent application Ser. No. 17/950,084. A single plant was discovered and selected indoors in a controlled environment from a batch of over 100 seeds.

'POI' produces massive purple, white, green, and yellow streaking resin-coated flowers. With massive flower clusters and very short internodal space, this cultivar is able to produce very high yields for both flower and hash production. Select phenotypes have been able to yield 100+ grams of manicured flower/ft2 of canopy space. A Sea of Green describes growing many plants together to form a continuous canopy. As opposed to growing individual large plants to fill a space, this method groups smaller plants tightly together while maintaining a uniform appearance.

It is a very hardy plant that is somewhat drought and bug resistant. Growing as much as 2+ inches per day with proper feed and environment.

'POI' unlike the parent, has a high degree of both tolerance to insects and fungus/molds. The growth pattern is tighter and faster, resulting in a higher yield within the same footprint. The scent and flavor of the finished product is much stronger and longer lasting than either parent and the side effects of inhalation are much more complex and intense than the mother plant. 'POI' is distinguished from its parents and related known cultivars (such as co-pending Plant patent application Ser. No. 17/950,086 'AFZ' and Plant patent application Ser. No. 17/950,085 'TZT') with a distinct and unique terpene profile and a heavy aroma and flavor of spumoni ice cream, dark chocolate, white truffle oil, lavender, fresh mint, black licorice, star arise, cardamon and vanilla extract. In addition, the selected plant expresses a higher concentration of anthocyanins present in both the leaves and stems as well as the harvested flowers. Onset of anthocyanins occurs several weeks sooner than either parent regardless of external temperature.

The below results are from an analysis of 1 selected phenotype for the claimed plant.

The cannabinoids and terpene analysis are from the dry flower of the selected plant. The method used was High-performance liquid and gas chromatography, otherwise known as HPLC and GCMS. The standard analytical method for these compounds.

TOTAL CANNABINOIDS 31.78% THC
TOTAL TERPENES 2.564%
0.286% Alpha Pinene
0.189% Beta Pinene
0.235% Myrcene
0.106% Limonene
<0.002% Ocimene
<0.002% Terpinolene
0.187% Linalool 1.128%
Caryophyllene 0.433%
Humulene

DETAILED BOTANICAL DESCRIPTION

Figure 1:
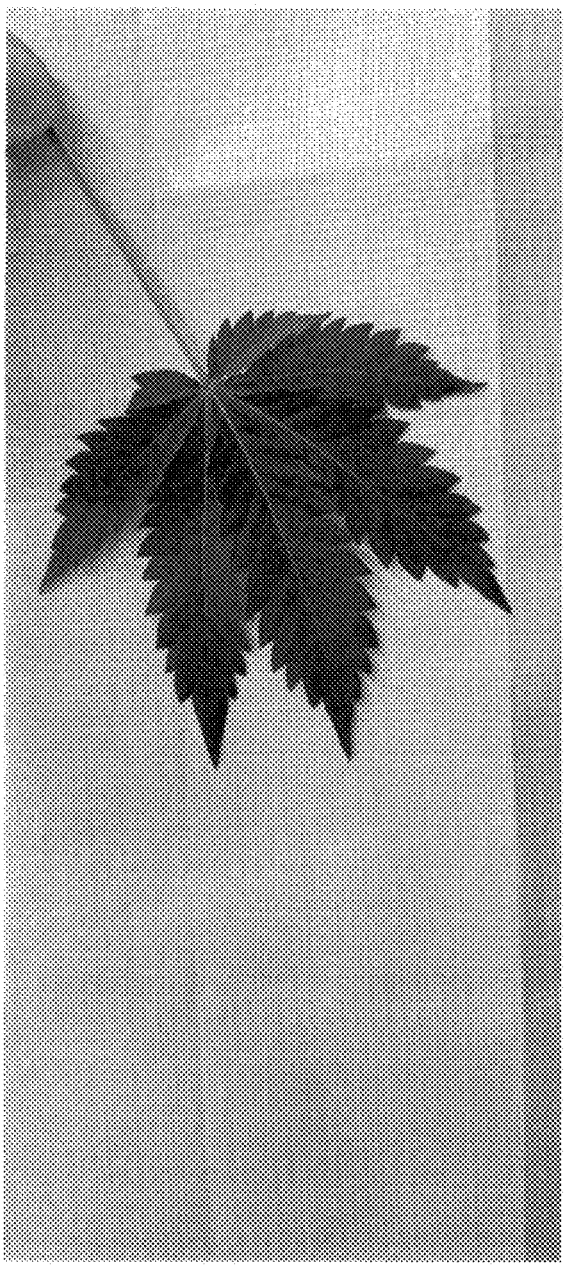
FIG. 1 is a view of the leaf is the upper surface of 'POI'.
Figure 2:
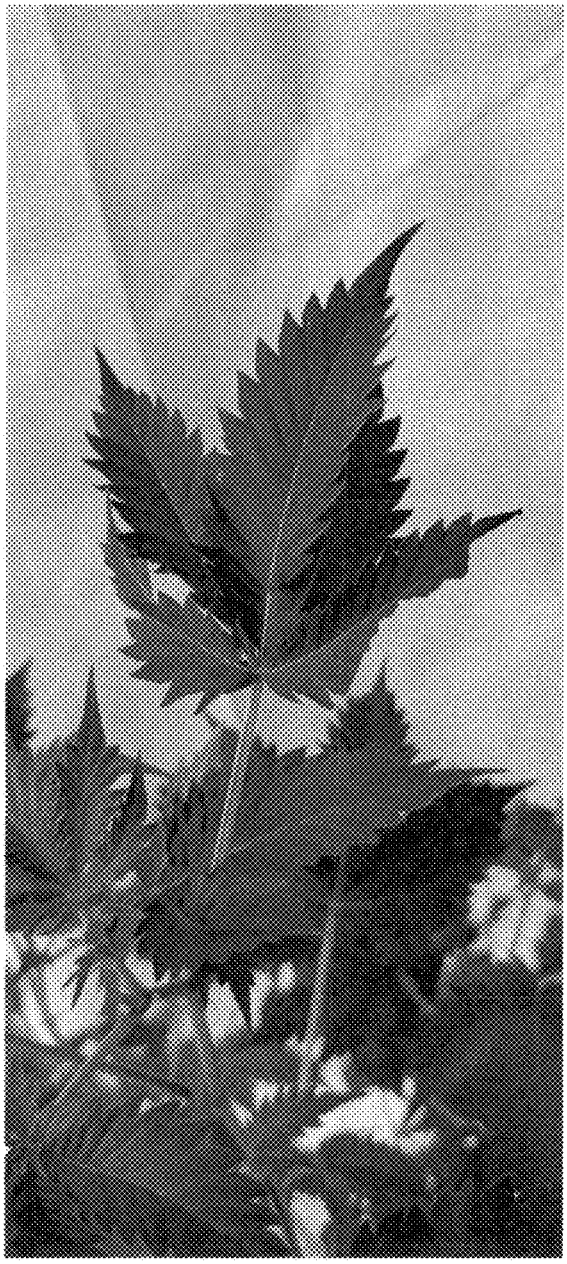
FIG. 2 is a view of several leaves and stems on a growing 'POI' plant.
Figure 3:
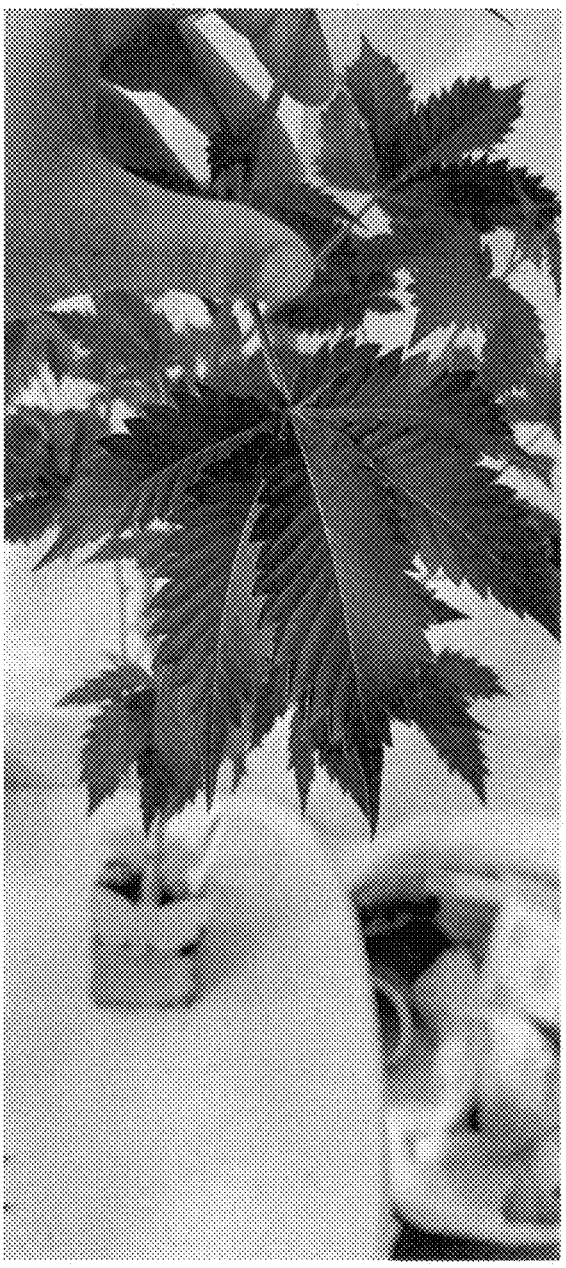
FIG. 3 is a view of leaves on a growing 'POI' plant.
Figure 4:
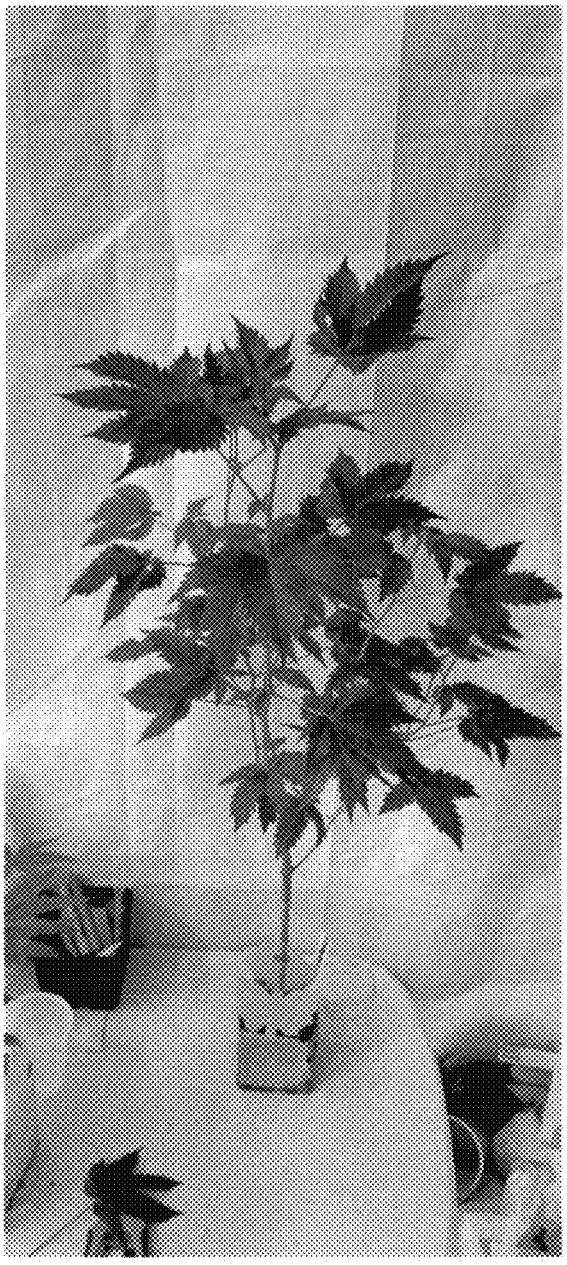
FIG. 4 is a view of a 'POI' plant.
Figure 5:
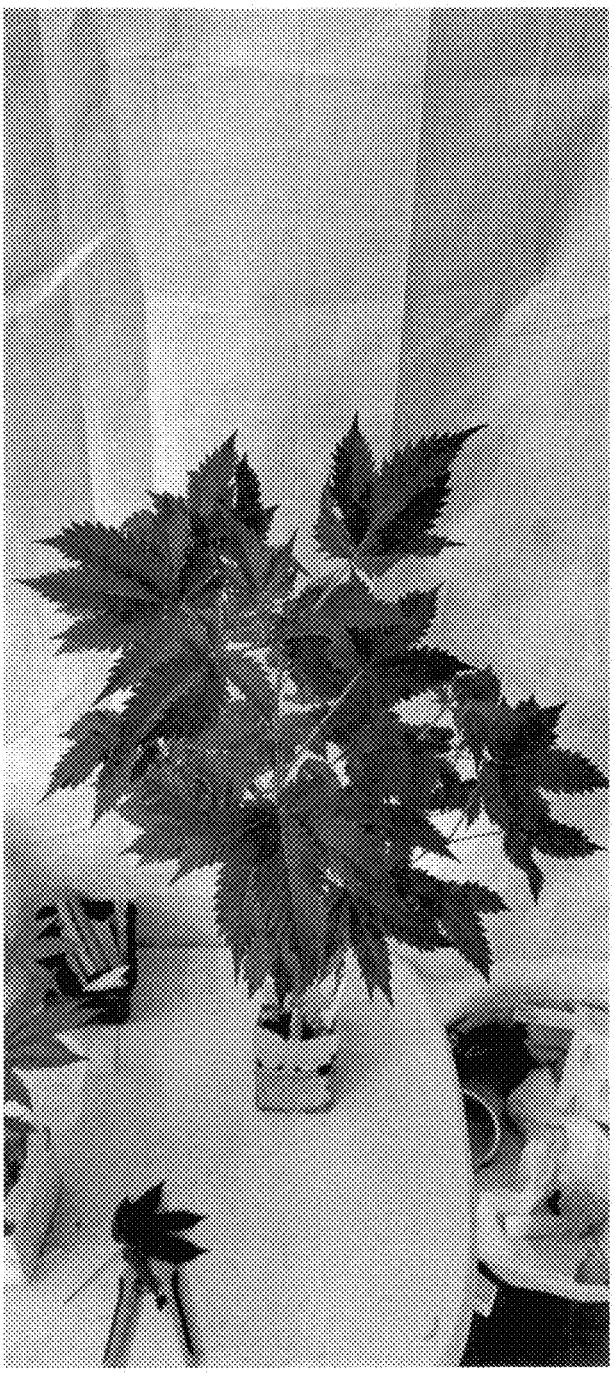
FIG. 5 is a view of a 'POI' plant.
Figure 6:
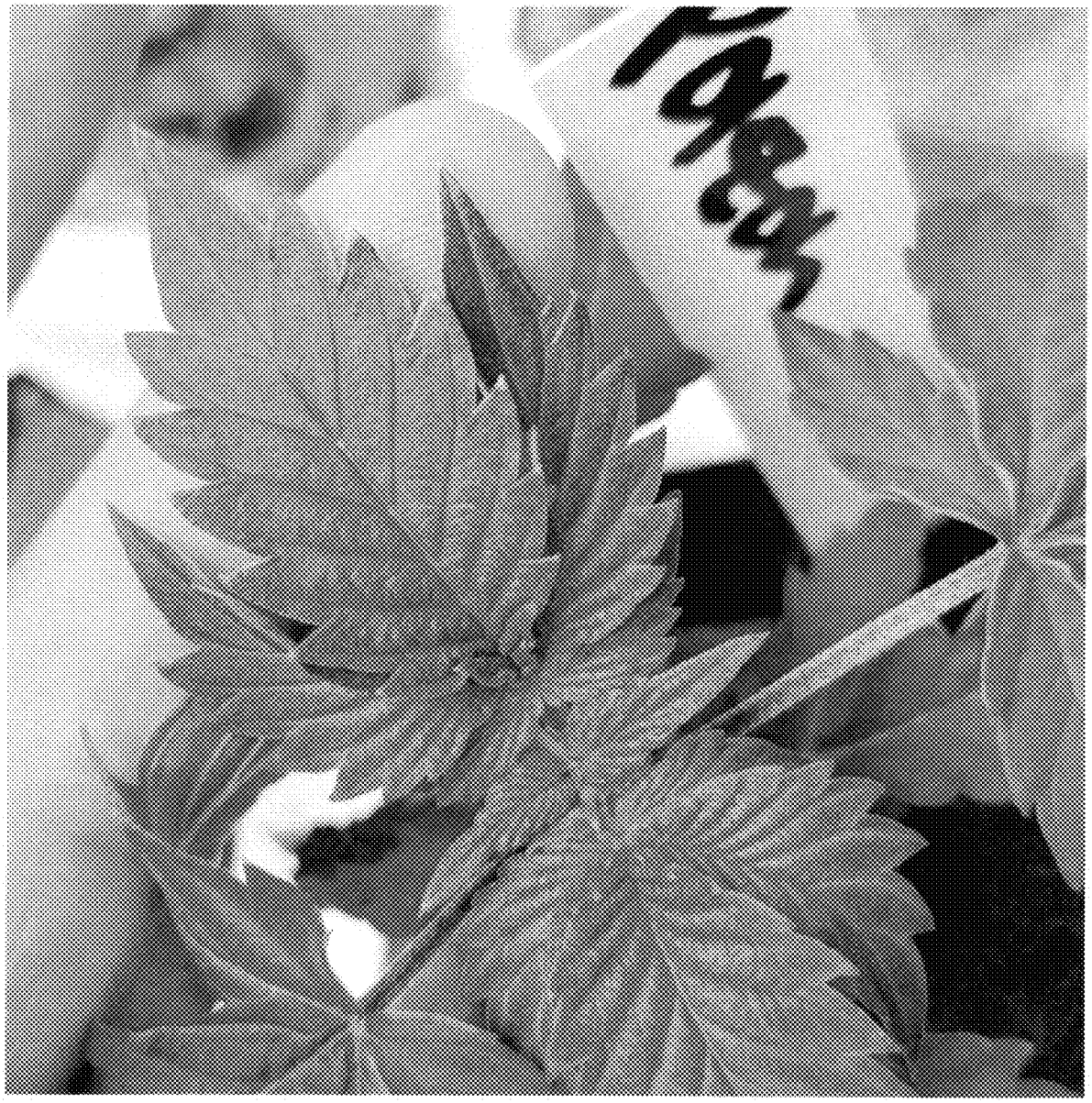
FIG. 6 is a view of young leaves and a meristem on a growing 'POI' plant.
Figure 7:
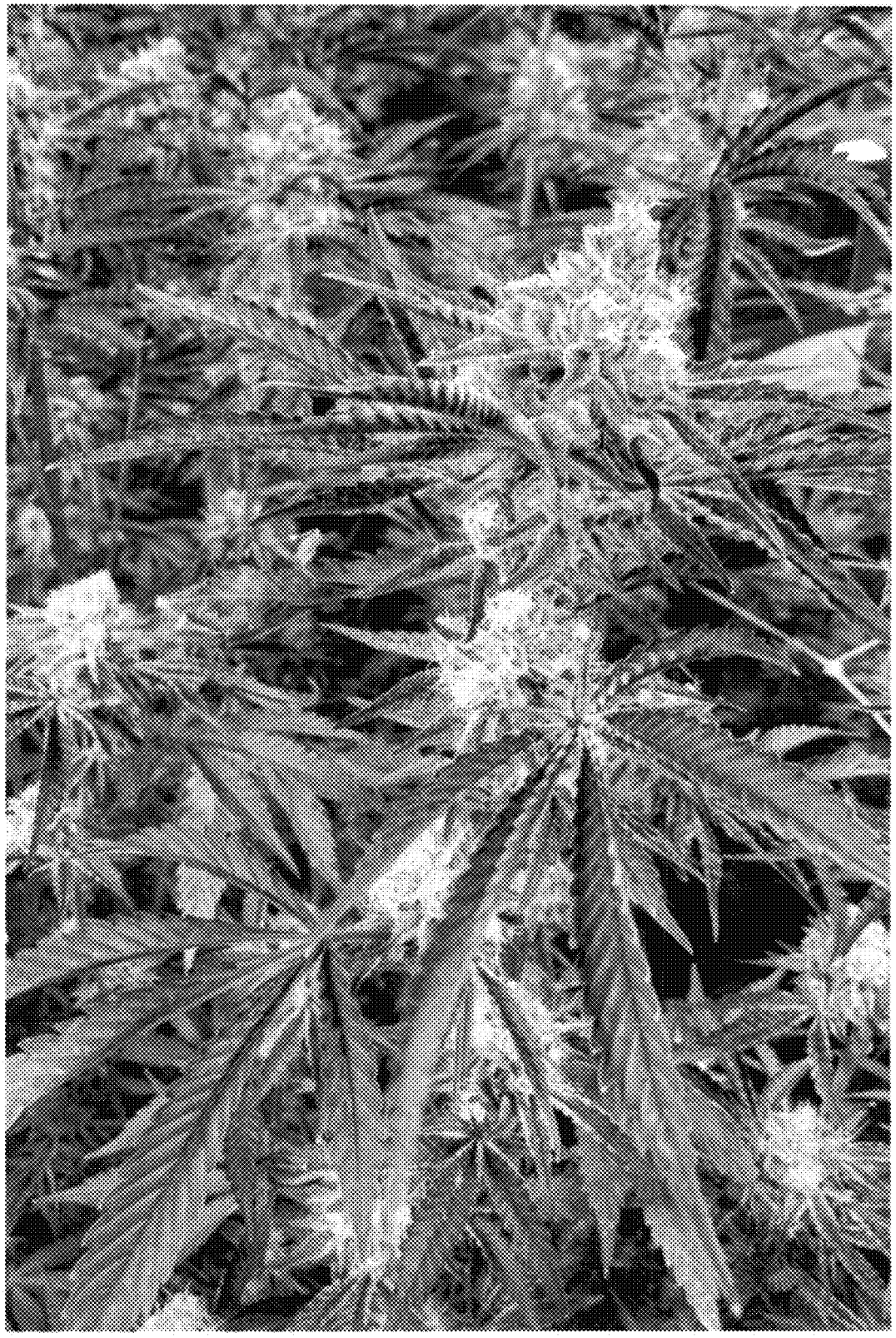
FIG. 7 is a view of the flowers of a 'POI' plant.

'POI' has not been observed under all possible environmental conditions, and the phenotype may vary significantly with variations in environment. The following observations, measurements, and comparisons describe this plant as grown at Mentone, Calif., when grown in the greenhouse, nursery or field, unless otherwise noted.

The color chart referenced is standard hexadecimal Web Pantone Color Chart well known to those of ordinary skill in Internet web site design.

The plant:

*Type* (*life form and habit*).—Herbaceous tap-rooted annual.

*Propagation*.—'POI' is asexually propagated via meristem Tissue Culture and Clonal propagation in Fallbrook, California.

*Leaves*.—Dark green PMS 350 with the bottom being light green PMS 368. The central leaflet is very broad, and each leaf overlaps the others and does not allow light to penetrate. They can be 8-10" long and have a total width of 8-11". The leaf is heavy gloss and shines bright in the sun or under HID or LED lighting appearing dark purple/brown PMS 276 and looking like glossy leather. The leaf ridges are very deep and wavy, the leaves do not lie flat but are shaped like a soundwave with equal parts up and down. The trichomes are mostly tall capitate stalked and are wet and gritty/sandy to the touch, releasing a heavy aroma of spumoni ice cream, dark chocolate, truffle oil, lavender, mint, black licorice and vanilla extract. The average number of leaflets is between many, 5-13 depending on the total plant size and health. The upper leaf surface is dark green PMS 350-PMS 3435 and purple PMS 276-2765 with the lower surface a light green PMS 361 with vibrant purple streaking PMS 2735 along the stem.

*Petioles*.—Typically, are medium to long, typically 4-6" long and 0.2-0.4" in diameter. The longer and older petioles will show heavy anthocyanin PMS 2735 production starting closer to the stem and moving out toward the leaf rachis. Trichomes are glandular with capitate stalked visible and bulbous trichomes and capitate-sessile trichomes are present all around. Petioles are dark green PMS 357 with purple anthocyanin PMS 2735 streaking and will turn fully purple PMS 2755-2765 within a few weeks of formation and during flowering.

*Stipules*.—Found at each node and are usually between 0.20-0.25" in length. They are medium PMS 348 to dark green PMS 350 (the older the darker) and spear-shaped and often accompanied by white pistils even during vegetative growth.

*Stem*.—The stem shape is a large, edged oval/octogon that has a minor zig-zag pattern as it grows (like most Zuchi progeny). Each node will begin to grow in the opposite direction of the previous node at the same growth angle. The internodal spacing is very short and compact. The stem is round and can reach a diameter of 1.5-2.2" when grown with a shallow groove depth and thick pith presence (full stems). There are capitate and bulbous visible trichomes growing on the stem. The stem color is light green PMS 368.

*Inforescence*.—The flowers are conal in shape, with the texture of a durian fruit. With a rounded base and sharp points emerging outward like a pinecone. The % of male vs female plants was approximately 50% female and 50% males in the selection process. There was <0.5% hermaphrodite expression from seed and after taking clones, the hermaphroditic expression was not seen again. The flowers are arranged in a tight checkered pattern up the stem. The flowers are dark purple PMS 2755 without any visible green coloration. The only visible green color PMS 361 is at the stem connecting the flower to the main stalk. There is a heavy presence and density of the large capitate stalked, glandula, and bulbous trichomes on every square millimeter of the flower and adjoining leaves. The fragrance and smoke/vapor flavors are a mix of spumoni ice cream, dark chocolate, truffle oil, lavender, mint, black licorice and vanilla extract.

*Bract*.—The bract is dark green PMS 357 to purple PMS 525 and 0.15" in diameter and 0.22-0.24" in length with white and yellow PMS 803 stigmas emerging from the center. They are covered with capitate-stalked trichomes and houses bulbous and capitate-sessile trichomes throughout.

*Bracteoles*.—Usually between 0.1-0.115" in length. They are slender spear-shaped and medium- dark green PMS 356-357 color.

*Stigma*.—Electric yellow PMS 803 and can reach up to 1.5-1.9 mm in size during the first 3 weeks of the flowering stage.

*Seeds*.—The seeds are round/oval in shape. Weight is low-very low and fully mature seeds are dark brown PMS 4625 with medium marbling.

*Height and spread*.—The average height can be modified depending on the volume of growing media and the irrigation frequency. In a 6×6×6 rockwool cube, being fed 1500-2250 ml per day a plant will average around 72-75" in height. The selected plant is grown in clusters with 9-12 plants per 16-24 ft2. A single 'POI' mother plant (used for asexual replication) can easily maintain a 25-30 ft2 area.

Classification: Cultivars of *Cannabis sativa*.

This cultivated line possesses intoxicating properties, and so the Subspecies *sativa* and its varieties (var. *sativa* and *spontanea*) are eliminated from consideration.

*Growth conditions*.—The plants are grown and are meant to be grown in a tightly controlled environment. They have been able to withstand temperatures above 105 degrees F. with 95% RH, as well as a RH of as low as 20%. Recent testing has shown that 'POI' is capable of thriving in a greenhouse with temperatures as low as 40 F with 85-95% RH.

*Market use*.—Market use for this product is medical and recreational *Cannabis* flower as well as extracts and infused goods. Individual plants grown with the above methods yield an average total plant wet weight of 2900-3200 g at harvest resulting in a dry flower weight of 150-200 grams.

All references cited in this specification, including but not limited to patent publications and non-patent literature, and references cited therein, are hereby incorporated by reference. The discussion of the references herein is intended merely to summarize the assertions made by the authors and no admission is made that any reference constitutes prior art. Applicants reserve the right to challenge the accuracy and pertinence of the cited references.

What is claimed is:

1. A new and distinct variety of *Cannabis* plant named 'POI', substantially as illustrated and described herein.

* * * * *